(12) United States Patent  (10) Patent No.: US 9,416,127 B2
Galley et al.  (45) Date of Patent: Aug. 16, 2016

(54) TRIAZOLE CARBOXAMIDES AND USES THEREOF

(71) Applicant: Hoffmann-La Roche Inc., Little Falls, NJ (US)

(72) Inventors: Guido Galley, Rheinfelden (DE); Cedric Ghellamallah, Marseilles (FR); Roger Norcross, Olsberg (CH); Philippe Pflieger, Schwoben (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/659,401

(22) Filed: Mar. 16, 2015

(65) Prior Publication Data

US 2015/0191458 A1  Jul. 9, 2015

Related U.S. Application Data

(63) Continuation of application No. PCT/EP2013/068968, filed on Sep. 13, 2013.

(30) Foreign Application Priority Data

Sep. 17, 2012  (EP) .................................. 12184613

(51) Int. Cl.
  C07D 413/12  (2006.01)
  C07D 401/12  (2006.01)
  C07D 403/12  (2006.01)
  A61K 31/5377  (2006.01)
  A61K 31/4192  (2006.01)
  A61K 31/4439  (2006.01)

(52) U.S. Cl.
  CPC .......... C07D 413/12 (2013.01); A61K 31/4192 (2013.01); A61K 31/4439 (2013.01); A61K 31/5377 (2013.01); C07D 401/12 (2013.01); C07D 403/12 (2013.01)

(58) Field of Classification Search
  CPC combination set(s) only.
  See application file for complete search history.

(56) References Cited

FOREIGN PATENT DOCUMENTS

WO  2011/076678  6/2011
WO  2012/168265  12/2012

OTHER PUBLICATIONS

International Search Report and Written Opinion on patentability for Patent Application No. PC/EP2013/068968, 2013.

*Primary Examiner* — Kristin Vajda

(57) ABSTRACT

The invention relates to compounds of formula

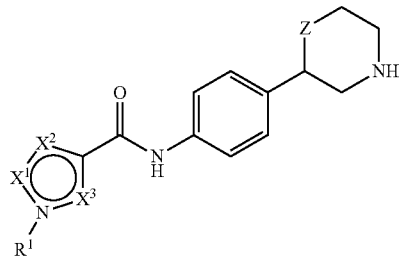

I wherein
$R^1$ is phenyl or pyridinyl, optionally substituted by halogen, lower alkyl, lower alkoxy, lower alkyl substituted by halogen and lower alkoxy substituted by halogen;
$X^1$ is —N= or CH;
$X^2$ is $CR^2$ or =N—;
$X^3$ is —N= or CH;
  with the proviso that only two of $X^1$, $X^2$ or $X^3$ are nitrogen;
wherein

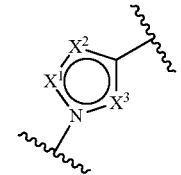

is a triazole group, selected from

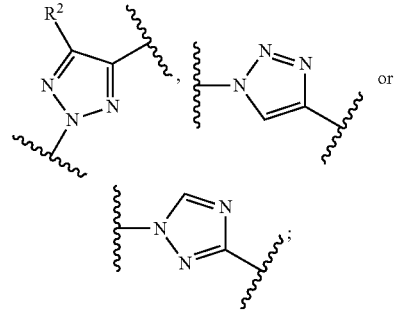

$R^2$ is hydrogen or lower alkyl;
Z is a bond, —O— or —CH$_2$—;
or to pharmaceutically suitable acid addition salts thereof
It has now been found that the compounds of formulas I have a good affinity to the trace amine associated receptors (TAARs), especially for TAAR1.
The compounds may be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

11 Claims, No Drawings

TRIAZOLE CARBOXAMIDES AND USES THEREOF

CROSS REFERENCE TO RELATED APPLICATIONS

This application is a continuation application and claims priority under 35 U.S.C. 365(c) to International Application No. PCT/EP2013/068968, filed on Sep. 13, 2013, which claims priority EP Application No. 12184613.3 filed on Sep. 17, 2012. The entire content of the applications referenced above are hereby incorporated by reference herein.

BACKGROUND OF INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gas. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors. Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol.* 1: *Trace Amines and the Brain. [Proceedings of a Study Group at the 14th Annual Meeting of the American College of Neuropsychoparmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

SUMMARY OF THE INVENTION

In one aspect, the present invention relates to compounds of formula

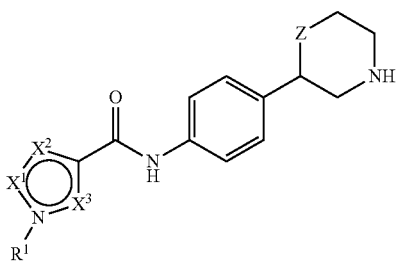

wherein
R[1] is phenyl or pyridinyl, optionally substituted by halogen, lower alkyl, lower alkoxy, lower alkyl substituted by halogen and lower alkoxy substituted by halogen;
X[1] is —N= or CH;
X[2] is CR[2] or =N—;
X[3] is —N= or CH;
with the proviso that only two of X[1], X[2] or X[3] are nitrogen;
wherein

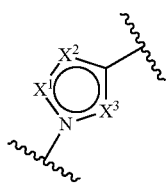

is a triazole group, selected from

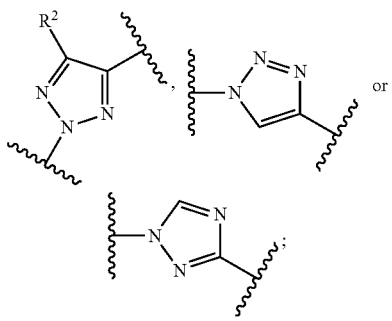

R[2] is hydrogen or lower alkyl;
Z is a bond, —O— or —CH$_2$—;
or to pharmaceutically suitable acid addition salts thereof.

The invention includes all racemic mixtures, all their corresponding enantiomers and/or optical isomers. In addition, all tautomeric forms of compounds of formula I are also encompassed by the present invention.

In another embodiment, the present inventions provide for pharmaceutical compositions comprising compounds of Formula I.

In another embodiment, the present invention provides for methods of treating disease associated with trace amine associated receptors.

DETAILED DESCRIPTION OF THE INVENTION

It has now been found that the compounds of formulas I have a good affinity to the trace amine associated receptors (TAARs), especially for TAAR1.

In one embodiment, the compounds may be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

In another embodiment, objects of the present invention are new compounds of formula I and their pharmaceutically acceptable salts, their use for the manufacture of medicaments for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety and attention deficit hyperactivity disorder (ADHD) and diabetes.

DEFINITIONS

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above and wherein at least one hydrogen atom is replaced by halogen.

As used herein, the term "lower alkoxy" denotes a group wherein the alkyl residue is as defined above and which is attached via an oxygen atom.

The term "halogen" denotes chlorine, iodine, fluorine and bromine.

As used herein, the term "lower alkoxy substituted by halogen" denotes an alkoxy group as defined above and wherein at least one hydrogen atom is replaced by halogen.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

One embodiment of the invention are compounds of formula IA

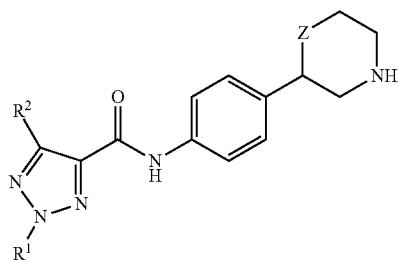

R$^1$ is phenyl or pyridinyl, optionally substituted by halogen, lower alkyl, lower alkoxy, lower alkyl substituted by halogen and lower alkoxy substituted by halogen;
R$^2$ is hydrogen or lower alkyl;
Z is a bond, —O— or —CH$_2$—;
or a pharmaceutically suitable acid addition salts thereof, for example the following compounds.
(S)—N-(4-(Morpholin-2-yl)phenyl)-2-phenyl-2H-1,2,3-triazole-4-carboxamide
(S)-5-Methyl-N-(4-(morpholin-2-yl)phenyl)-2-phenyl-2H-1,2,3-triazole-4-carboxamide
(S)-2-(4-Chlorophenyl)-N-(4-(morpholin-2-yl)phenyl)-2H-1,2,3-triazole-4-carboxamide
(R)-5-Methyl-N-(4-(morpholin-2-yl)phenyl)-2-phenyl-2H-1,2,3-triazole-4-carboxamide
(R)—N-(4-(Morpholin-2-yl)phenyl)-2-phenyl-2H-1,2,3-triazole-4-carboxamide
(S)-2-(4-Fluorophenyl)-N-(4-(morpholin-2-yl)phenyl)-2H-1,2,3-triazole-4-carboxamide
(S)—N-(4-(Morpholin-2-yl)phenyl)-2-(4-(trifluoromethyl)phenyl)-2H-1,2,3-triazole-4-carboxamide
(S)-2-(3-Fluorophenyl)-N-(4-(morpholin-2-yl)phenyl)-2H-1,2,3-triazole-4-carboxamide
(S)-2-(3-Chlorophenyl)-N-(4-(morpholin-2-yl)phenyl)-2H-1,2,3-triazole-4-carboxamide
(S)—N-(4-(Morpholin-2-yl)phenyl)-2-(3-(trifluoromethyl)phenyl)-2H-1,2,3-triazole-4-carboxamide
(S)—N-(4-(Morpholin-2-yl)phenyl)-2-(4-(trifluoromethoxy)phenyl)-2H-1,2,3-triazole-4-carboxamide
(S)-2-(4-(Difluoromethoxy)phenyl)-N-(4-(morpholin-2-yl)phenyl)-2H-1,2,3-triazole-4-carboxamide
(S)—N-(4-(Morpholin-2-yl)phenyl)-2-p-tolyl-2H-1,2,3-triazole-4-carboxamide hydrochloride
(S)-2-(4-Methoxyphenyl)-N-(4-(morpholin-2-yl)phenyl)-2H-1,2,3-triazole-4-carboxamide
(S)-2-(4-Ethoxyphenyl)-N-(4-(morpholin-2-yl)phenyl)-2H-1,2,3-triazole-4-carboxamide
(S)—N-(4-(Morpholin-2-yl)phenyl)-2-m-tolyl-2H-1,2,3-triazole-4-carboxamide hydrochloride
(S)—N-(4-(Morpholin-2-yl)phenyl)-2-(3-(trifluoromethoxy)phenyl)-2H-1,2,3-triazole-4-carboxamide
(S)-2-(3-Methoxyphenyl)-N-(4-(morpholin-2-yl)phenyl)-2H-1,2,3-triazole-4-carboxamide
(S)-2-(3-Methoxyphenyl)-N-(4-(morpholin-2-yl)phenyl)-2H-1,2,3-triazole-4-carboxamide
(RS)-2-Phenyl-N-(4-(pyrrolidin-3-yl)phenyl)-2H-1,2,3-triazole-4-carboxamide or
2-Phenyl-N-(4-(piperidin-3-yl)phenyl)-2H-1,2,3-triazole-4-carboxamide.

One further embodiment of the invention are compounds of formula IB

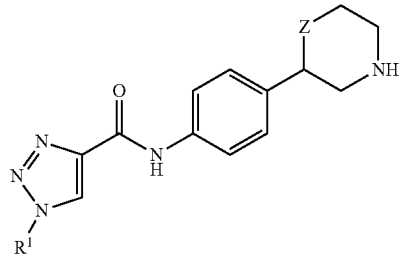

wherein
R$^1$ is phenyl or pyridinyl, optionally substituted by halogen, lower alkyl, lower alkoxy, lower alkyl substituted by halogen and lower alkoxy substituted by halogen;
Z is a bond, —O— or —CH$_2$—;
or a pharmaceutically suitable acid addition salts thereof, for example the following compounds
(S)-1-(4-(Difluoromethoxy)phenyl)-N-(4-(morpholin-2-yl)phenyl)-1H-1,2,3-triazole-4-carboxamide
(S)-1-(4-Fluorophenyl)-N-(4-(morpholin-2-yl)phenyl)-1H-1,2,3-triazole-4-carboxamide
(S)-1-(3-Fluorophenyl)-N-(4-(morpholin-2-yl)phenyl)-1H-1,2,3-triazole-4-carboxamide
(S)—N-(4-(Morpholin-2-yl)phenyl)-1-(4-(trifluoromethoxy)phenyl)-1H-1,2,3-triazole-4-carboxamide
(S)—N-(4-(Morpholin-2-yl)phenyl)-1-p-tolyl-1H-1,2,3-triazole-4-carboxamide hydrochloride
(S)-1-(4-Methoxyphenyl)-N-(4-(morpholin-2-yl)phenyl)-1H-1,2,3-triazole-4-carboxamide
(S)-1-(4-Ethoxyphenyl)-N-(4-(morpholin-2-yl)phenyl)-1H-1,2,3-triazole-4-carboxamide
(S)—N-(4-(Morpholin-2-yl)phenyl)-1-m-tolyl-1H-1,2,3-triazole-4-carboxamide hydrochloride
(S)-1-(3-Methoxyphenyl)-N-(4-(morpholin-2-yl)phenyl)-1H-1,2,3-triazole-4-carboxamide
(S)-1-(3-Ethoxyphenyl)-N-(4-(morpholin-2-yl)phenyl)-1H-1,2,3-triazole-4-carboxamide
(S)—N-(4-(Morpholin-2-yl)phenyl)-1-(3-(trifluoromethoxy)phenyl)-1H-1,2,3-triazole-4-carboxamide
(S)-1-(3-(Difluoromethoxy)phenyl)-N-(4-(morpholin-2-yl)phenyl)-1H-1,2,3-triazole-4-carboxamide or
(RS)-1-(4-(Difluoromethoxy)phenyl)-N-(4-(pyrrolidin-3-yl)phenyl)-1H-1,2,3-triazole-4-carboxamide.

One further embodiment of the invention are compounds of formula IC

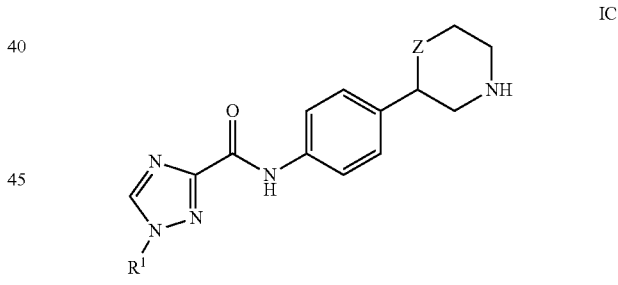

wherein
R$^1$ is phenyl or pyridinyl, optionally substituted by halogen, lower alkyl, lower alkoxy, lower alkyl substituted by halogen and lower alkoxy substituted by halogen;
Z is a bond, —O— or —CH$_2$—;
or a pharmaceutically suitable acid addition salts thereof, for example the following compound (S)-1-(4-(Difluoromethoxy)phenyl)-N-(4-(morpholin-2-yl)phenyl)-1H-1,2,4-triazole-3-carboxamide.

The present compounds of formula I and their pharmaceutically acceptable salts can be prepared by methods known in the art, for example, by processes described below, which process comprises
a) cleaving off the N-protecting group from compounds of formula

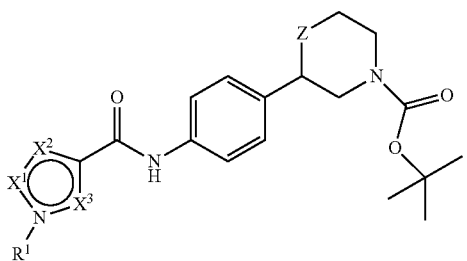

to form a compound of formula

I

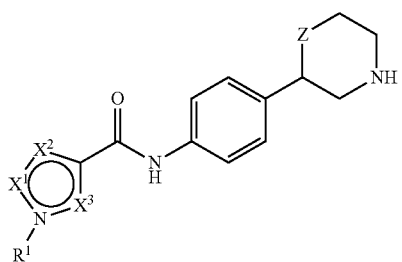

wherein the definitions are as described above, and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1 and in the description of 36 specific examples. The skills required for carrying out the reactions and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

General Procedure:

Scheme 1

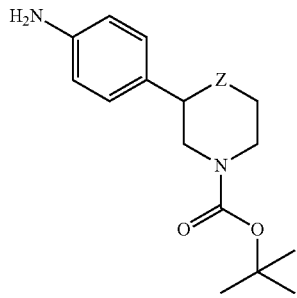

2

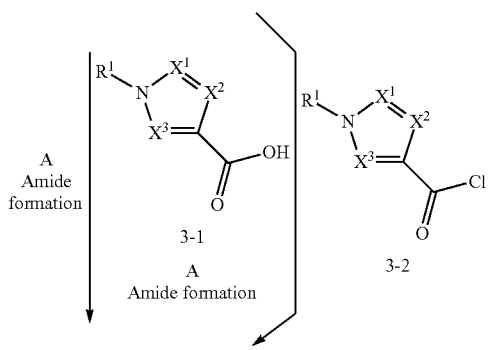

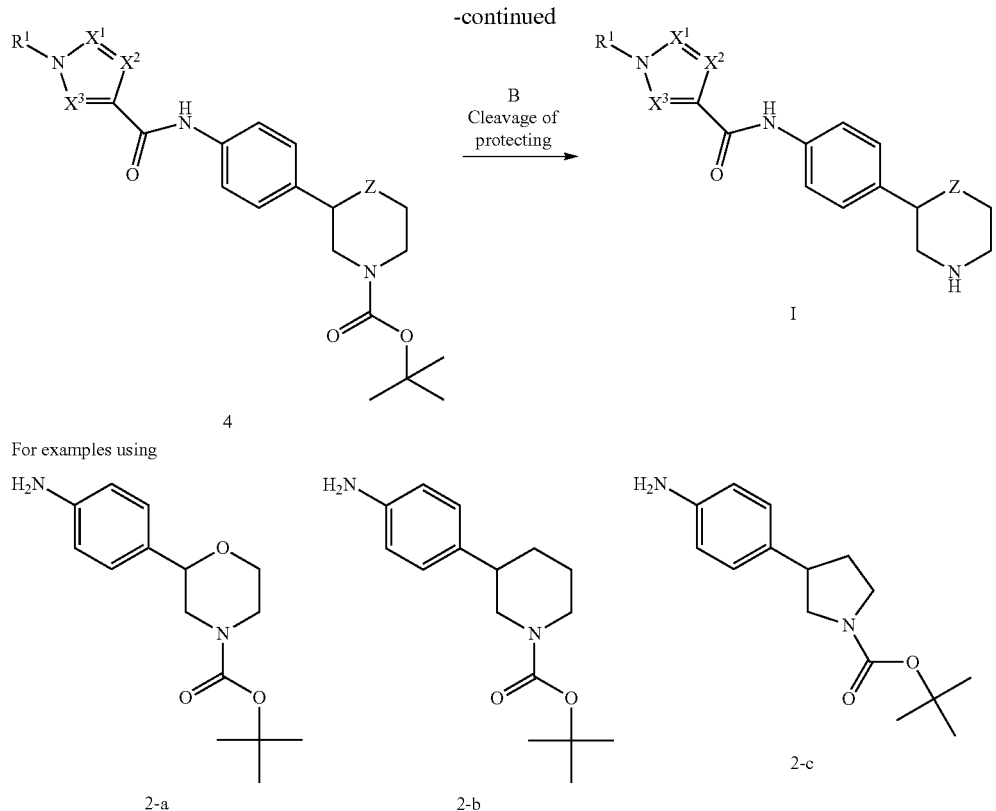

For examples using 2-a    2-b    2-c

The substituents are as described above.

Step A:

Amide formation can be accomplished by a coupling reaction between an amine 2 and acid chloride compounds 3-2 in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine. Examples of appropriate amines 2 include N-protected morpholine derivatives such as 2-a [CAS 1002726-96-6], piperidine derivatives such as 2-b [CAS 875798-79-1], pyrrolidine derivatives such as 2-c [CAS 908334-28-1]. Preferred conditions are triethylamine in THF at room temperature for 18 hours.

If desired, the acyl chloride compound 3-2 may be prepared in situ from the corresponding carboxylic acid 3-1 by treatment with oxalyl chloride or 1-chloro-N,N,2-trimethypropenylamine in halogenated solvents such as dichloromethane or 1,2-dichloroethane or ethereal solvents such as diethyl ether, dioxane, THF, DME or TBME in the presence of a catalyst such as DMF. Preferred conditions are dichloromethane at room temperature for 1 hour.

Alternatively, amide formation can be accomplished by a coupling reaction between an amine 2 and carboxylic acids 3-1 in the presence of a coupling reagent such as DCC, EDC, TBTU, HBTU or HATU in the presence of an organic base such as triethylamine, N,N-diisopropylethylamine or N-methylmorpholine in halogenated solvents such as DMF, dichloromethane or 1,2-dichloroethane or ethereal solvents such as diethyl ether, dioxane, THF, DME or TBME.

Preferred conditions are BTU with N-methylmorpholine in DMF at 60° C. for 18 hours.

Step B:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, dioxane, MeOH, EtOH or $H_2O$ at 0 to 80° C. Preferred conditions are HCl in dioxane at 60° C. for 1-20 h.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

Example 1

(S)—N-(4-(Morpholin-2-yl)phenyl)-2-phenyl-2H-1,2,3-triazole-4-carboxamide hydrochloride

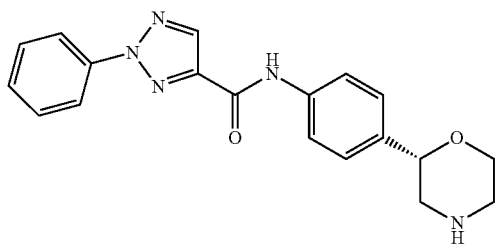 [SMILES: O=C(Nc1ccc([C@H]2CNCCO2)cc1)c1cnn(-c2ccccc2)n1]

a) Preparation of (S)-tert-Butyl 2-(4-(2-phenyl-2H-1,2,3-triazole-4-carboxamido)phenyl)morpholine-4-carboxylate In a 25 mL round-bottomed flask, 2-phenyl-2H-1,2,3-triazole-4-carboxylic acid (CAS 13306-99-5) (59.8 mg, 316 µmol, Eq: 1.1), (S)-tert-butyl 2-(4-aminophenyl)morpholine-4-carboxylate (80 mg, 287 µmol, Eq: 1.00), N-methylmorpholine (87.2 mg, 94.8 µl, 862 µmol, Eq: 3) and HBTU (164 mg, 431 µmol, Eq: 1.5) were combined with DMF (2 ml) to give a yellow solution. The reaction mixture was stirred overnight at 60° C. The mixture was poured into water (10 ml) and extracted twice with EtOAc. The organic layers were washed with NaHCO₃, brine, dried over MgSO₄, filtered and concentrated in vacuo to give a brown crude mixture. This mixture was diluted with ether, stirred for 15 minutes and the suspension was filtered. The resulting solid was washed several times with ether to afford the desired compound as a light-yellow solid (35 mg, 27.1%).
MS (ISP): 394.0 ([M+H]⁺-isobutene).

b) (S)—N-(4-(Morpholin-2-yl)phenyl)-2-phenyl-2H-1,2,3-triazole-4-carboxamide hydrochloride To a solution of (S)-tert-butyl 2-(4-(2-phenyl-2H-1,2,3-triazole-4-carboxamido)phenyl)morpholine-4-carboxylate (30 mg, 66.7 µmol, Eq: 1.00) in dioxane (2 ml) was added 4 M HCl in dioxane (250 µl, 1.00 mmol, Eq: 15). The reaction mixture was stirred at 60° C. for 48 hours. To the mixture was added 2 ml of diethyl ether and stirred for 15 min at room temperature. The mixture was filtered and concentrated in high vacuum to give the expected HCl salt as a light-yellow solid (24 mg, 93.2%). MS (ISP): 350.3 ([M+H]⁺).

Preparation of (S)-tert-Butyl 2-(4-aminophenyl)morpholine-4-carboxylate

Step a) (S)-2-(4-Bromophenyl)morpholine 2.27 g (RS)-2-(4-Bromo-phenyl)-morpholine (CAS-1131220-82-0) were separated on a Chiralpak IA HPLC column (8×32 cm) using n-heptane/ethanol (1:11)+0.1% DEA.

(S)-2-(4-bromo-phenyl)-morpholine: fractions collected from 7.6 min to 9.4 min. Yield 0.97 g (42.9%) with 97.4% ee
(R)-2-(4-bromo-phenyl)-morpholine: fractions collected from 9.8 min to 13.9 min Yield 0.99 g (43.6%) with 97.4% ee Step b) (S)-tert-butyl 2-(4-bromophenyl)morpholine-4-carboxylate (S)-2-(4-Bromo-phenyl)-morpholine (36.3 g, 150 mmol) and N,N-diisopropylethylamine (23.3 g, 31.4 ml, 180 mmol) in THF (360 ml) were treated with di-tert-butyl dicarbonate (39.3 g, 180 mmol). The reaction mixture was stirred for 17 h at rt, concentrated in vacuo, diluted with ethyl acetate, washed with 1M citric acid (2×100 ml), dried over magnesium sulfate, filtered and concentrated in vacuo. The crude material was crystallized from hexane to afford 47.1 g (92%) (S)-tert-butyl 2-(4-bromophenyl)morpholine-4-carboxylate as an off-white solid. MS (ISP): 344.1 ([M+H]⁺).

Step c) (S)-tert-Butyl 2-(4-(diphenylmethylene-amino)phenyl)morpholine-4-carboxylate (S)-tert-Butyl 2-(4-bromophenyl)morpholine-4-carboxylate (47 g, 137 mmol), diphenylmethanimine (29.9 g, 27.6 m, 165 mmol), BINAP (6.41 g, 10.3 mmol) and Pd₂(dba)₃ (3.14 g, 3.43 mmol) were dissolved under argon in dry and de-aerated toluene (940 ml) and treated with sodium tert-butoxide (18.5 g, 192 mmol). The dark brown mixture was stirred at 90° C. for 18 h. The yellow/brown reaction mixture was diluted with toluene (700 ml), cooled to rt and extracted twice with water. The organic layer was separated, dried over magnesium sulfate and concentrated in vacuo. The crude product was diluted with 300 ml hexane, stirred for 1 h and filtered off, leading to an orange solid (68 g) which was purified by column chromatography (1.3 kg silicagel, 20% ethylacetate/heptane). The combined and concentrated fractions were suspended in hexane, stirred for 17 h, filtered off and dried under high vacuum, to yield 54.1 g (89%) yellow solid. MS (ISP): 443.3 ([M+H]⁺).

Step d) (S)-tert-Butyl 2-(4-aminophenyl)morpholine-4-carboxylate

A suspension of (S)-tert-butyl 2-(4-(diphenylmethylene-amino)phenyl)morpholine-4-carboxylate (54.1 g, 122 mmol), ammonium formate (116 g, 1.83 mol) and 5% Pd/C (6.5 g, 3.06 mmol) in methanol (930 ml) was stirred at 60° C. for 2 h. The reaction mixture was filtered and concentrated. The residue was dissolved in ethyl acetate and water. The organic phase was extracted twice with 0.5 M HCl. The combined aqueous phases were basified with 2 M NaOH and extracted twice with DCM. The organic phases were dried over magnesium sulfate, filtered and dried in vacuo, to yield 31.95 g off-white solid. MS (ISP): 279.1 ([M+H]⁺).

Example 2

(S)-5-Methyl-N-(4-(morpholin-2-yl)phenyl)-2-phenyl-2H-1,2,3-triazole-4-carboxamide hydrochloride

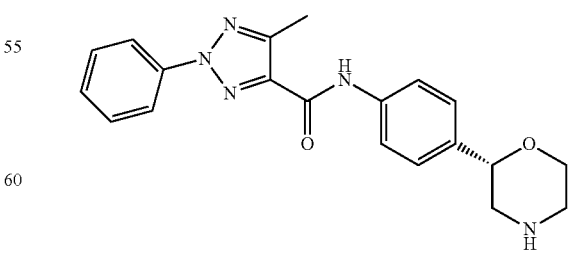

The title compound was prepared in analogy to Example 1 step a) using 5-methyl-2-phenyl-2H-1,2,3-triazole-4-carboxylic acid (CAS 22300-56-7) instead of 2-phenyl-2H-1,2,3-triazole-4-carboxylic acid.

Step b): To a solution of (S)-tert-butyl 2-(4-(5-methyl-2-phenyl-2H-1,2,3-triazole-4-carboxamido)phenyl)morpholine-4-carboxylate (106 mg, 229 μmol, Eq: 1.00) in dioxane (298 μl) was added 4 M HCl in dioxane (858 μl, 3.43 mmol, Eq: 15). The reaction mixture was stirred at 60° C. overnight. To the mixture was added 2 ml of dioxane and stirred for 15 min at room temperature. The mixture was filtered and concentrated under high vacuum to give the expected HCl salt as a white solid (82 mg, 90%)

White solid. MS (ISP): 364.4 ([M+H]+).

Example 3

(S)-1-(4-(Difluoromethoxy)phenyl)-N-(4-(morpholin-2-yl)phenyl)-1H-1,2,3-triazole-4-carboxamide hydrochloride

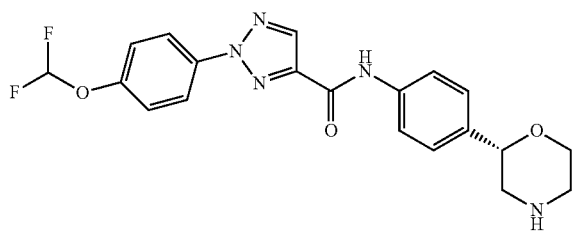 [SMILES: O=C(Nc1ccc([C@H]2CNCCO2)cc1)c1cnn(-c2ccc(OC(F)F)cc2)n1]

The title compound was prepared in analogy to Example 2 using 1-(4-(difluoromethoxy)phenyl)-1H-1,2,3-triazole-4-carboxylic acid (CAS 1096995-13-9) instead of 5-methyl-2-phenyl-2H-1,2,3-triazole-4-carboxylic acid in step a).

White solid. MS (ISP): 416.1 ([M+H]+).

Example 4

(S)-1-(4-Fluorophenyl)-N-(4-(morpholin-2-yl)phenyl)-1H-1,2,3-triazole-4-carboxamide hydrochloride

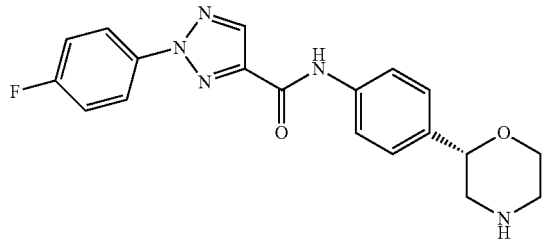 [SMILES: O=C(Nc1ccc([C@H]2CNCCO2)cc1)c1cnn(-c2ccc(F)cc2)n1]

The title compound was prepared in analogy to Example 2 using 1-(4-fluorophenyl)-1H-1,2,3-triazole-4-carboxylic acid (CAS 214541-35-2) instead of 5-methyl-2-phenyl-2H-1,2,3-triazole-4-carboxylic acid in step a).

White solid. MS (ISP): 368.0 ([M+H]+).

Example 5

(S)-1-(3-Fluorophenyl)-N-(4-(morpholin-2-yl)phenyl)-1H-1,2,3-triazole-4-carboxamide hydrochloride

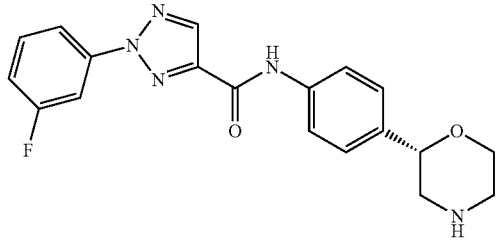 [SMILES: O=C(Nc1ccc([C@H]2CNCCO2)cc1)c1cnn(-c2cccc(F)c2)n1]

The title compound was prepared in analogy to Example 2 using 1-(3-fluorophenyl)-1H-1,2,3-triazole-4-carboxylic acid (CAS 944905-84-4) instead of 5-methyl-2-phenyl-2H-1,2,3-triazole-4-carboxylic acid in step a).

Light yellow solid. MS (ISP): 368.0 ([M+H]+).

Example 6

(S)-2-(4-Chlorophenyl)-N-(4-(morpholin-2-yl)phenyl)-2H-1,2,3-triazole-4-carboxamide hydrochloride

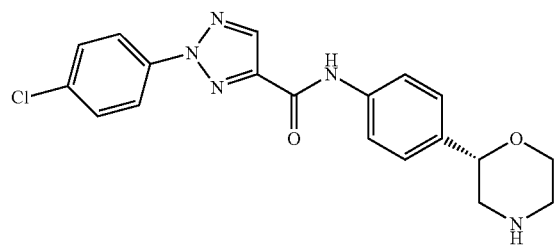 [SMILES: O=C(Nc1ccc([C@H]2CNCCO2)cc1)c1cnn(-c2ccc(Cl)cc2)n1]

The title compound was prepared in analogy to Example 2 using 2-(4-chlorophenyl)-2H-1,2,3-triazole-4-carboxylic acid (CAS 89522-59-8) instead of 5-methyl-2-phenyl-2H-1,2,3-triazole-4-carboxylic acid in step a).

Light yellow solid. MS (ISP): 384.2 ([M+H]+).

Example 7

(R)-5-Methyl-N-(4-(morpholin-2-yl)phenyl)-2-phenyl-2H-1,2,3-triazole-4-carboxamide hydrochloride

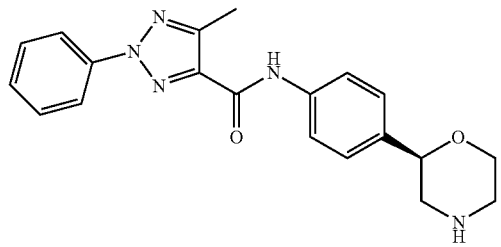 [SMILES: Cc1nn(-c2ccccc2)nc1C(=O)Nc1ccc([C@@H]2CNCCO2)cc1]

The title compound was prepared in analogy to Example 2 using 5-methyl-2-phenyl-2H-1,2,3-triazole-4-carboxylic acid (CAS 22300-56-7) instead of 5-methyl-2-phenyl-2H-1,2,3-triazole-4-carboxylic acid and (R)-tert-butyl 2-(4-aminophenyl)morpholine-4-carboxylate instead of (S)-tert-butyl 2-(4-aminophenyl)morpholine-4-carboxylate in step a).

Light yellow solid. MS (ISP): 364.1 ([M+H]+).

Example 8

(R)—N-(4-(Morpholin-2-yl)phenyl)-2-phenyl-2H-1,2,3-triazole-4-carboxamide hydrochloride

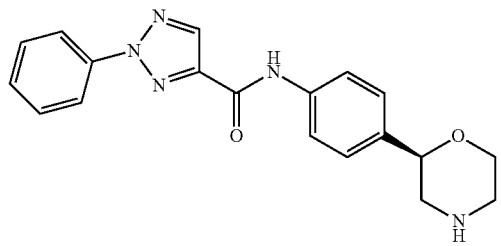 [SMILES: O=C(Nc1ccc([C@@H]2CNCCO2)cc1)c1cnn(-c2ccccc2)n1]

The title compound was prepared in analogy to Example 2 using 2-phenyl-2H-1,2,3-triazole-4-carboxylic acid (CAS 13306-99-5) instead of 5-methyl-2-phenyl-2H-1,2,3-triazole-4-carboxylic acid and (R)-tert-butyl 2-(4-aminophenyl)

morpholine-4-carboxylate instead of (S)-tert-butyl 2-(4-aminophenyl)morpholine-4-carboxylate in step a).
Yellow solid. MS (ISP): 350.3 ([M+H]+).

Example 9

(S)-2-(4-Fluorophenyl)-N-(4-(morpholin-2-yl)phenyl)-2H-1,2,3-triazole-4-carboxamide hydrochloride

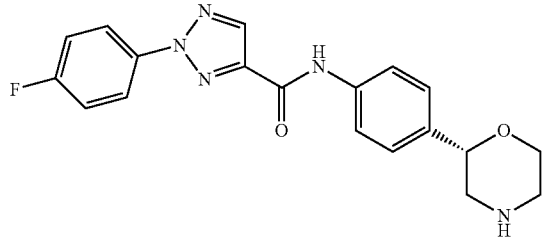 [SMILES: O=C(Nc1ccc([C@H]2CNCCO2)cc1)c1cnn(-c2ccc(F)cc2)n1]

The title compound was prepared in analogy to Example 2 using 2-(4-fluorophenyl)-2H-1,2,3-triazole-4-carboxylic acid (CAS 833-60-3) instead of 5-methyl-2-phenyl-2H-1,2,3-triazole-4-carboxylic acid in step a).
White solid. MS (ISP): 368.2 ([M+H]+).

Example 10

(S)—N-(4-(Morpholin-2-yl)phenyl)-2-(4-(trifluoromethyl)phenyl)-2H-1,2,3-triazole-4-carboxamide hydrochloride

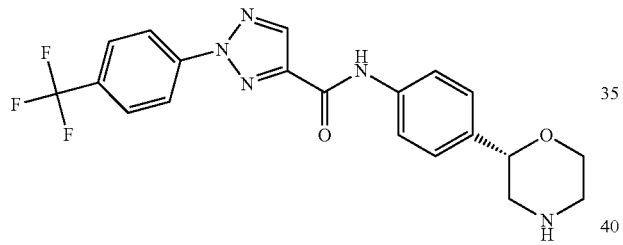

The title compound was prepared in analogy to Example 2 using 2-(4-(trifluoromethyl)phenyl)-2H-1,2,3-triazole-4-carboxylic acid (CAS 1368530-38-4) instead of 5-methyl-2-phenyl-2H-1,2,3-triazole-4-carboxylic acid in step a).
Light yellow solid. MS (ISP): 418.3 ([M+H]+).

Example 11

(S)-2-(3-Fluorophenyl)-N-(4-(morpholin-2-yl)phenyl)-2H-1,2,3-triazole-4-carboxamide hydrochloride

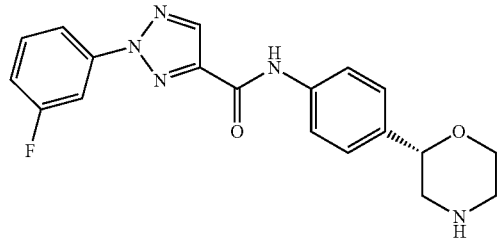 [SMILES: O=C(Nc1ccc([C@H]2CNCCO2)cc1)c1cnn(-c2cccc(F)c2)n1]

The title compound was prepared in analogy to Example 2 using 2-(3-fluorophenyl)-2H-1,2,3-triazole-4-carboxylic acid (CAS 833-54-5) instead of 5-methyl-2-phenyl-2H-1,2,3-triazole-4-carboxylic acid in step a).
White solid. MS (ISP): 368.2 ([M+H]+).

Example 12

(S)-2-(3-Chlorophenyl)-N-(4-(morpholin-2-yl)phenyl)-2H-1,2,3-triazole-4-carboxamide hydrochloride

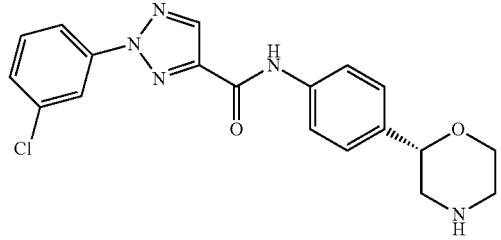 [SMILES: O=C(Nc1ccc([C@H]2CNCCO2)cc1)c1cnn(-c2cccc(Cl)c2)n1]

The title compound was prepared in analogy to Example 2 using 2-(3-chlorophenyl)-2H-1,2,3-triazole-4-carboxylic acid (CAS 90839-69-3) instead of 5-methyl-2-phenyl-2H-1,2,3-triazole-4-carboxylic acid in step a).
Off-white solid. MS (ISP): 384.2 ([M+H]+).

Example 13

(S)—N-(4-(Morpholin-2-yl)phenyl)-2-(3-(trifluoromethyl)phenyl)-2H-1,2,3-triazole-4-carboxamide hydrochloride

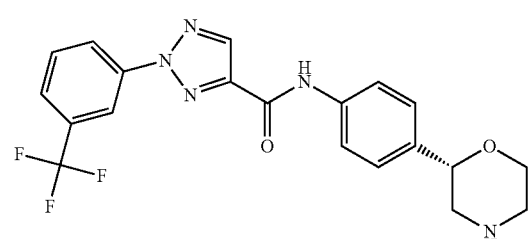

The title compound was prepared in analogy to Example 2 using 2-(3-(trifluoromethyl)phenyl)-2H-1,2,3-triazole-4-carboxylic acid (CAS 1368509-73-2) instead of 5-methyl-2-phenyl-2H-1,2,3-triazole-4-carboxylic acid in step a).
White solid. MS (ISP): 418.3 ([M+H]+).

Example 14

(S)—N-(4-(Morpholin-2-yl)phenyl)-1-(4-(trifluoromethoxy)phenyl)-1H-1,2,3-triazole-4-carboxamide hydrochloride

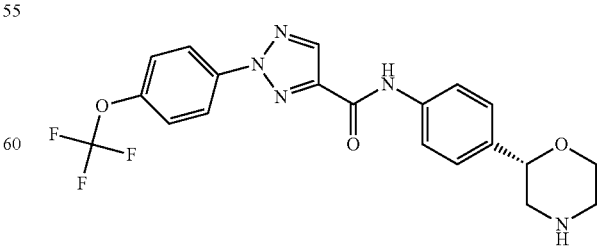

The title compound was prepared in analogy to Example 2 using 1-(4-(trifluoromethoxy)phenyl)-1H-1,2,3-triazole-4- carboxylic acid (CAS 1338653-72-7) instead of 5-methyl-2-phenyl-2H-1,2,3-triazole-4-carboxylic acid in step a).

Light yellow solid. MS (ISP): 434.3 ([M+H]⁺).

Example 15

(S)—N-(4-(Morpholin-2-yl)phenyl)-2-(4-(trifluoromethoxy)phenyl)-2H-1,2,3-triazole-4-carboxamide hydrochloride

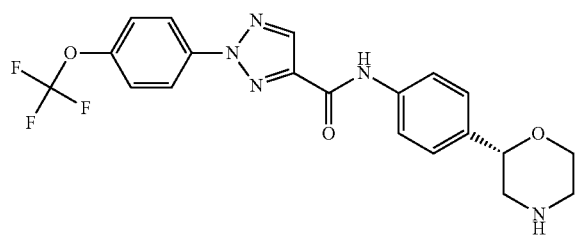 [SMILES: O=C(Nc1ccc([C@H]2CNCCO2)cc1)c1cnn(-c2ccc(OC(F)(F)F)cc2)n1]

The title compound was prepared in analogy to Example 2 using 2-(4-(trifluoromethoxy)phenyl)-2H-1,2,3-triazole-4-carboxylic acid instead of 5-methyl-2-phenyl-2H-1,2,3-triazole-4-carboxylic acid in step a).

White solid. MS (ISP): 434.3 ([M+H]⁺).

Preparation of 2-(4-(trifluoromethoxy)phenyl)-2H-1,2,3-triazole-4-carboxylic acid Step a) Ethyl 2-(4-(trifluoromethoxy)phenyl)-2H-1,2,3-triazole-4-carboxylate Ethyl 2H-1,2,3-triazole-4-carboxylate (CAS 1084802-21-0) (250 mg, 1.77 mmol, Eq: 1.00), 4-(trifluoromethoxy)phenylboronic acid (730 mg, 3.54 mmol, Eq: 2) and diacetoxy copper (644 mg, 3.54 mmol, Eq: 2) were dissolved in DMA (8.86 ml). Then pyridine (560 mg, 572 µl, 7.09 mmol, Eq: 4) was added and the reaction mixture was stirred at rt for 48 hours. Water and ethyl acetate were added to the reaction mixture. The organic layer was separated, washed with brine, dried over MgSO4 and evaporated. The crude material was purified by silica gel flash chromatography to yield a white solid (129 mg, 24%). MS (ISP): 302.1 ([M+H]⁺).

Step b) 2-(4-(Trifluoromethoxy)phenyl)-2H-1,2,3-triazole-4-carboxylic acid

To a solution of ethyl 2-(4-(trifluoromethoxy)phenyl)-2H-1,2,3-triazole-4-carboxylate (127 mg, 422 µmol, Eq: 1.00) in THF (5 ml) and MeOH (1.00 ml) was added LiOH 1M (843 µl, 843 µmol, Eq: 2). The mixture was stirred overnight. To the residue was added water and 1 N HCl (pH:1), this aqueous phase was extracted two times with ethyl acetate, the resulting organic layers were combined and washed with brine, then dried over MgSO4, filtered and concentrated to give the desired compound (94 mg, 81.6%) as a white solid.

Example 16

(S)-2-(4-(Difluoromethoxy)phenyl)-N-(4-(morpholin-2-yl)phenyl)-2H-1,2,3-triazole-4-carboxamide hydrochloride

The title compound was prepared in analogy to Example 15 using 4-(difluoromethoxy)phenylboronic acid instead of 4-(trifluoromethoxy)phenylboronic acid in step a).

Light yellow solid. MS (ISP): 416.3 ([M+H]⁺).

Example 17

(S)—N-(4-(Morpholin-2-yl)phenyl)-1-p-tolyl-1H-1,2,3-triazole-4-carboxamide hydrochloride

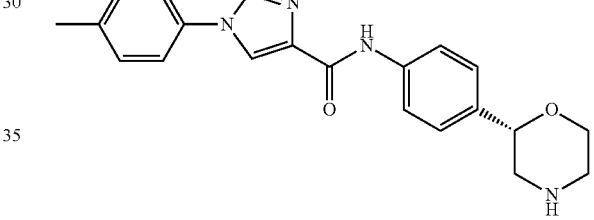

The title compound was prepared in analogy to Example 2 using 1-p-tolyl-1H-1,2,3-triazole-4-carboxylic acid (CAS 113934-31-9) instead of 5-methyl-2-phenyl-2H-1,2,3-triazole-4-carboxylic acid in step a).

White solid. MS (ISP): 364.2 ([M+H]⁺).

Example 18

(S)—N-(4-(Morpholin-2-yl)phenyl)-2-p-tolyl-2H-1,2,3-triazole-4-carboxamide hydrochloride

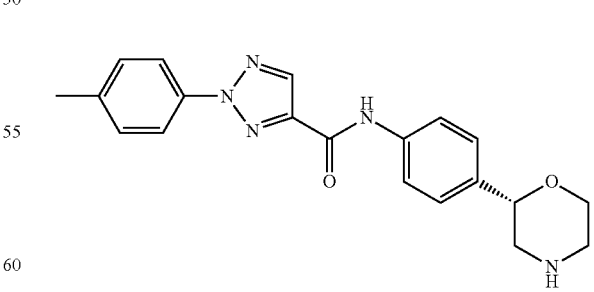

The title compound was prepared in analogy to Example 2 using 2-p-tolyl-2H-1,2,3-triazole-4-carboxylic acid (CAS 69059-60-5) instead of 5-methyl-2-phenyl-2H-1,2,3-triazole-4-carboxylic acid in step a).

White solid. MS (ISP): 364.2 ([M+H]⁺).

Example 19

(S)-1-(4-Methoxyphenyl)-N-(4-(morpholin-2-yl)phenyl)-1H-1,2,3-triazole-4-carboxamide hydrochloride

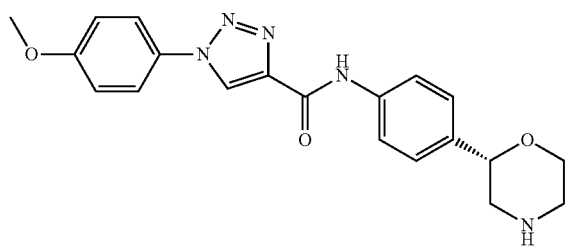 [SMILES: COc1ccc(-n2cc(C(=O)Nc3ccc([C@H]4CNCCO4)cc3)nn2)cc1]

The title compound was prepared in analogy to Example 2 using 1-(4-methoxyphenyl)-1H-1,2,3-triazole-4-carboxylic acid (CAS 4916-13-6) instead of 5-methyl-2-phenyl-2H-1,2,3-triazole-4-carboxylic acid in step a).

White solid. MS (ISP): 380.3 ([M+H]$^+$).

Example 20

(S)-2-(4-Methoxyphenyl)-N-(4-(morpholin-2-yl)phenyl)-2H-1,2,3-triazole-4-carboxamide hydrochloride

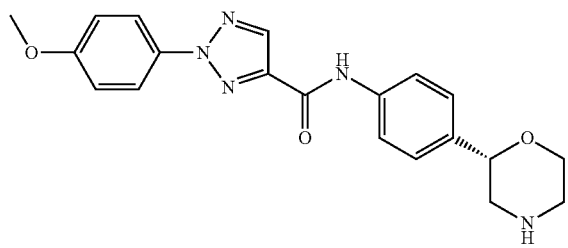 [SMILES: COc1ccc(-n2ncc(C(=O)Nc3ccc([C@H]4CNCCO4)cc3)n2)cc1]

The title compound was prepared in analogy to Example 2 using 2-(4-methoxyphenyl)-2H-1,2,3-triazole-4-carboxylic acid (CAS 90946-76-2) instead of 5-methyl-2-phenyl-2H-1,2,3-triazole-4-carboxylic acid in step a).

White solid. MS (ISP): 380.2 ([M+H]$^+$).

Example 21

(S)-1-(4-Ethoxyphenyl)-N-(4-(morpholin-2-yl)phenyl)-1H-1,2,3-triazole-4-carboxamide hydrochloride

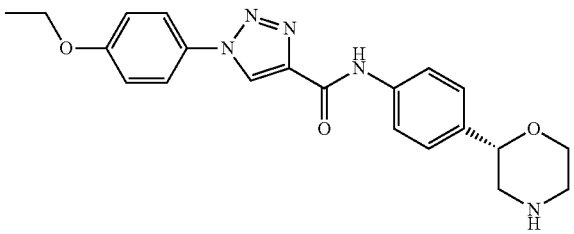 [SMILES: CCOc1ccc(-n2cc(C(=O)Nc3ccc([C@H]4CNCCO4)cc3)nn2)cc1]

The title compound was prepared in analogy to Example 2 using 1-(4-ethoxyphenyl)-1H-1,2,3-triazole-4-carboxylic acid (CAS 1042534-41-7) instead of 5-methyl-2-phenyl-2H-1,2,3-triazole-4-carboxylic acid in step a).

White solid. MS (ISP): 394.2 ([M+H]$^+$).

Example 22

(S)-2-(4-Ethoxyphenyl)-N-(4-(morpholin-2-yl)phenyl)-2H-1,2,3-triazole-4-carboxamide hydrochloride

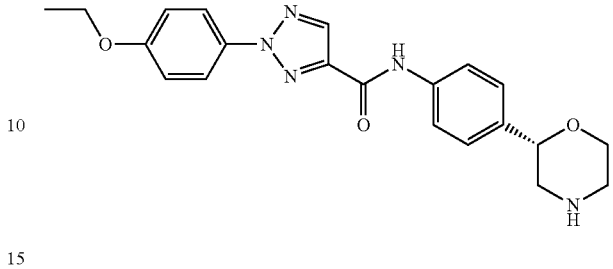

The title compound was prepared in analogy to Example 2 using 2-(4-ethoxyphenyl)-2H-1,2,3-triazole-4-carboxylic acid (CAS 1368754-17-9) instead of 5-methyl-2-phenyl-2H-1,2,3-triazole-4-carboxylic acid in step a).

White solid. MS (ISP): 394.2 ([M+H]$^+$).

Example 23

(S)—N-(4-(Morpholin-2-yl)phenyl)-2-m-tolyl-2H-1,2,3-triazole-4-carboxamide hydrochloride

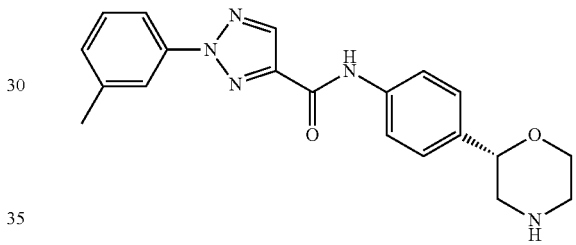

The title compound was prepared in analogy to Example 2 using 2-m-tolyl-2H-1,2,3-triazole-4-carboxylic acid (CAS 1042655-56-0) instead of 5-methyl-2-phenyl-2H-1,2,3-triazole-4-carboxylic acid in step a).

White solid. MS (ISP): 364.3 ([M+H]$^+$).

Example 24

(S)—N-(4-(Morpholin-2-yl)phenyl)-1-m-tolyl-1H-1,2,3-triazole-4-carboxamide hydrochloride

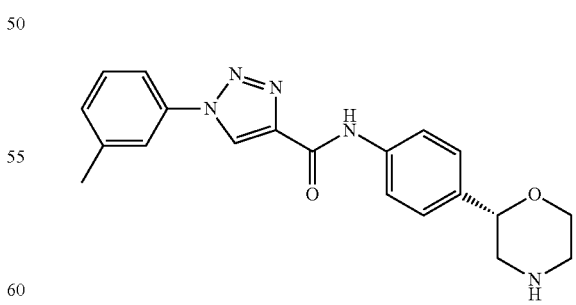

The title compound was prepared in analogy to Example 2 using 1-m-tolyl-1H-1,2,3-triazole-4-carboxylic acid (CAS 944901-55-7) instead of 5-methyl-2-phenyl-2H-1,2,3-triazole-4-carboxylic acid in step a).

White solid. MS (ISP): 364.3 ([M+H]$^+$).

Example 25

(S)-1-(3-Methoxyphenyl)-N-(4-(morpholin-2-yl)phenyl)-1H-1,2,3-triazole-4-carboxamide hydrochloride

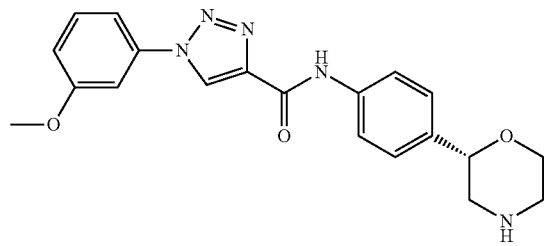 [SMILES: COc1cccc(-n2cc(C(=O)Nc3ccc([C@H]4CNCCO4)cc3)nn2)c1]

The title compound was prepared in analogy to Example 2 using 1-(3-methoxyphenyl)-1H-1,2,3-triazole-4-carboxylic acid (CAS 944901-61-5) instead of 5-methyl-2-phenyl-2H-1,2,3-triazole-4-carboxylic acid in step a).
White solid. MS (ISP): 380.3 ([M+H]$^+$).

Example 26

(S)-1-(3-Ethoxyphenyl)-N-(4-(morpholin-2-yl)phenyl)-1H-1,2,3-triazole-4-carboxamide hydrochloride

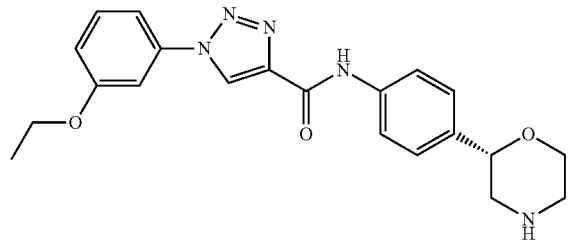 [SMILES: CCOc1cccc(-n2cc(C(=O)Nc3ccc([C@H]4CNCCO4)cc3)nn2)c1]

The title compound was prepared in analogy to Example 2 using 1-(3-ethoxyphenyl)-1H-1,2,3-triazole-4-carboxylic acid (CAS 1275299-39-2) instead of 5-methyl-2-phenyl-2H-1,2,3-triazole-4-carboxylic acid in step a).
White solid. MS (ISP): 394.2 ([M+H]$^+$).

Example 27

(S)—N-(4-(Morpholin-2-yl)phenyl)-1-(3-(trifluoromethoxy)phenyl)-1H-1,2,3-triazole-4-carboxamide hydrochloride

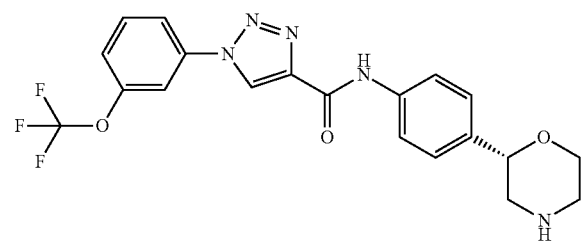 [SMILES: O=C(Nc1ccc([C@H]2CNCCO2)cc1)c1cn(-c2cccc(OC(F)(F)F)c2)nn1]

The title compound was prepared in analogy to Example 2 using 1-(3-(trifluoromethoxy)phenyl)-1H-1,2,3-triazole-4-carboxylic acid (CAS 1340992-22-4) instead of 5-methyl-2-phenyl-2H-1,2,3-triazole-4-carboxylic acid in step a).
White solid. MS (ISP): 434.1 ([M+H]$^+$).

Example 28

(S)—N-(4-(Morpholin-2-yl)phenyl)-2-(3-(trifluoromethoxy)phenyl)-2H-1,2,3-triazole-4-carboxamide hydrochloride

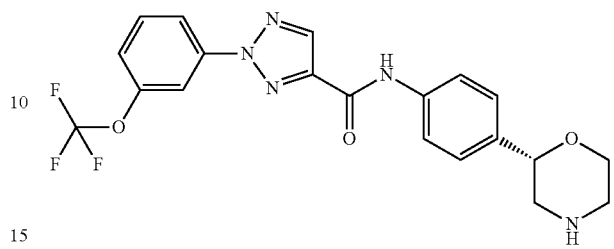

The title compound was prepared in analogy to Example 15 using 3-(trifluoromethoxy)phenylboronic acid instead of 4-(trifluoromethoxy)phenylboronic acid in step a).
White solid. MS (ISP): 434.3 ([M+H]$^+$).

Example 29

(S)-1-(3-(Difluoromethoxy)phenyl)-N-(4-(morpholin-2-yl)phenyl)-1H-1,2,3-triazole-4-carboxamide hydrochloride

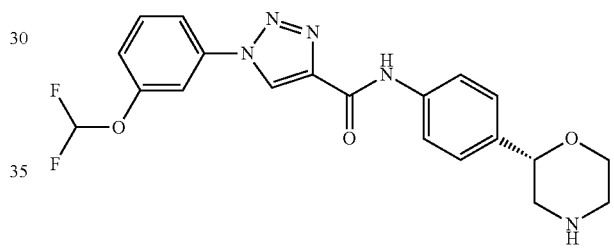

The title compound was prepared in analogy to Example 15 using 3-(difluoromethoxy)phenylboronic acid instead of 4-(trifluoromethoxy)phenylboronic acid in step a).
White solid. MS (ISP): 416.2 ([M+H]$^+$).

Example 30

(S)-2-(3-Methoxyphenyl)-N-(4-(morpholin-2-yl)phenyl)-2H-1,2,3-triazole-4-carboxamide hydrochloride

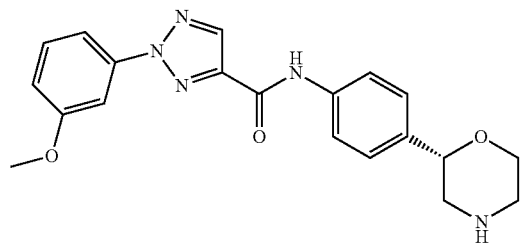 [SMILES: COc1cccc(-n2ncc(C(=O)Nc3ccc([C@H]4CNCCO4)cc3)n2)c1]

The title compound was prepared in analogy to Example 2 using 2-(3-methoxyphenyl)-2H-1,2,3-triazole-4-carboxylic acid (CAS 36401-47-5) instead of 5-methyl-2-phenyl-2H-1,2,3-triazole-4-carboxylic acid in step a).
White solid. MS (ISP): 380.5 ([M+H]$^+$).

Example 31

(S)-2-(3-Methoxyphenyl)-N-(4-(morpholin-2-yl)phenyl)-2H-1,2,3-triazole-4-carboxamide hydrochloride

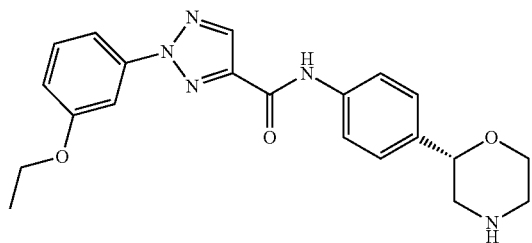 [SMILES: CCOc1cccc(-n2ncc(C(=O)Nc3ccc([C@H]4CNCCO4)cc3)n2)c1]

The title compound was prepared in analogy to Example 15 using 3-ethoxyphenylboronic acid instead of 4-(trifluoromethoxy)phenylboronic acid in step a).

White solid. MS (ISP): 394.2 ([M+H]$^+$).

Example 32

(S)-1-(4-(Difluoromethoxy)phenyl)-N-(4-(morpholin-2-yl)phenyl)-1H-1,2,4-triazole-3-carboxamide hydrochloride

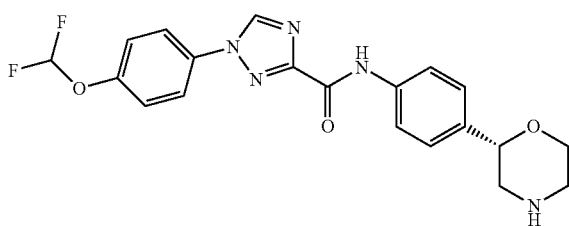 [SMILES: O=C(Nc1ccc([C@H]2CNCCO2)cc1)c1ncn(-c2ccc(OC(F)F)cc2)n1]

a) 1-(4-(Difluoromethoxy)phenyl)-1H-1,2,4-triazole-3-carboxylic acid 4-(Difluoromethoxy)aniline (1 g, 6.28 mmol) was dissolved in aqueous hydrochloric acid (12%, 7.35 ml, 25.1 mmol). The solution was cooled to 0° C. and sodium nitrite (434 mg, 6.28 mmol) dissolved in water (2 ml) was slowly added at a temperature below 5° C. After being stirred at 0° C. for 30 min, a solution of ethyl isocyanoacetate (711 mg, 6.28 mmol) and sodium acetate (5.16 g, 62.8 mmol) in MeOH (20 ml) and water (6 ml) was slowly added dropwise at the same temperature. The reaction mixture was stirred for 2 h at 0° C. The solvent was evaporated, 1 M hydrochloric acid was added and the mixture was extracted with ethyl acetate. The organic phase was washed with sodium bicarbonate solution and brine and dried with MgSO$_4$. After chromatography (Silica gel, 40 g, 50% EtOAc in heptane) 220 mg ester was obtained that was dissolved in a mixture of tetrahydrofuran (2 ml), methanol (1 ml) and water (1 ml). Lithium hydroxide hydrate (97.8 mg, 2.33 mmol) was added and the solution was heated to 80° C. for 2 h. The solvent was removed under reduced pressure. The residue obtained was dissolved in 1 M hydrochloric acid and the solution was extracted with ethyl acetate twice. The combined organic layers were dried over MgSO$_4$ and evaporated. The orange solid was recrystallized in a mixture of heptane and ethyl acetate (4:1). 121 mg (7%) of an off-white solid was obtained. 1H NMR (300 MHz, CDCl$_3$) ∂ ppm: 7.34 (t, 1H; J=73 Hz), 7.41 (d, 2H; J=8.7 Hz), 7.95 (d, 2H; J=8.7 Hz), 9.38 (s, 1H).

b) (S)-tert-Butyl 2-(4-(1-(4-(difluoromethoxy)phenyl)-1H-1,2,4-triazole-3-carboxamido)phenyl)morpholine-4-carboxylate (S)-tert-Butyl 2-(4-aminophenyl)morpholine-4-carboxylate (109 mg, 0.39 mmol), 1-(4-(difluoromethoxy)phenyl)-1H-1,2,4-triazole-3-carboxylic acid (100 mg, 0.39 mmol), HBTU (167 mg, 0.44 mmol) and N-methylmorpholine (119 mg, 130 µl, 1.18 mmol) were combined with DMF (2 ml) to give a light yellow solution. The reaction mixture was stirred at 60° C. overnight.

Water and ethyl acetate were added to the reaction mixture. The organic layer was separated, washed with brine, dried over MgSO$_4$ and evaporated. The crude material was purified by flash chromatography (Silica gel, 10 g, 50% to 60% EtOAc in heptane) to yield a white solid (189 mg, 94%). MS (ISP): 459.1 (100%, [M-tBu+H]$^+$), 515.2 (30%, [M+H]$^+$).

c) (S)-1-(4-(Difluoromethoxy)phenyl)-N-(4-(morpholin-2-yl)phenyl)-1H-1,2,4-triazole-3-carboxamide hydrochloride (S)-tert-Butyl 2-(4-(1-(4-(difluoromethoxy)phenyl)-1H-1,2,4-triazole-3-carboxamido)phenyl)morpholine-4-carboxylate (180 mg, 0.35 mmol) was dissolved in dioxane (1.3 ml) and a solution of HCl in dioxane (4M, 1.3 ml, 5.2 mmol) was added. The reaction mixture was stirred for 90 min at 60° C. After cooling ether was added, the solid was filtered off, washed with ether and dried in vacuo at 60° C. to afford (S)-1-(4-(difluoromethoxy)phenyl)-N-(4-(morpholin-2-yl)phenyl)-1H-1,2,4-triazole-3-carboxamide hydrochloride (123 mg, 78%) as a white solid. MS (ISP): 416.4 ([M+H]$^+$).

Example 33

(RS)-1-(4-(Difluoromethoxy)phenyl)-N-(4-(pyrrolidin-3-yl)phenyl)-1H-1,2,3-triazole-4-carboxamide

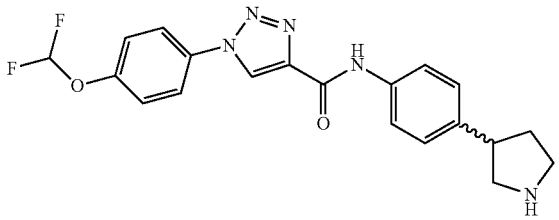 [SMILES: O=C(Nc1ccc(C2CCNC2)cc1)c1cn(-c2ccc(OC(F)F)cc2)nn1]

The title compound was obtained in analogy to example 3 using tert-butyl 3-(4-aminophenyl)pyrrolidine-1-carboxylate instead of (S)-tert-butyl 2-(4-aminophenyl)morpholine-4-carboxylate. Yellow solid. MS (ISP): 400.16 ([M+H]$^+$).

Example 34

(RS)-2-Phenyl-N-(4-(pyrrolidin-3-yl)phenyl)-2H-1,2,3-triazole-4-carboxamide

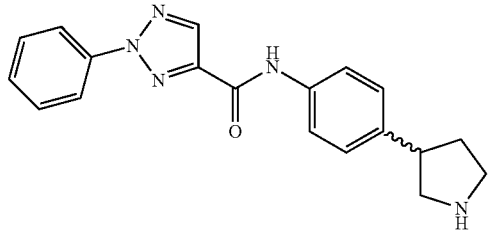 [SMILES: O=C(Nc1ccc(C2CCNC2)cc1)c1cnn(-c2ccccc2)n1]

The title compound was obtained in analogy to example 1 using tert-butyl 3-(4-aminophenyl)pyrrolidine-1-carboxylate instead of (S)-tert-butyl 2-(4-aminophenyl)morpholine-4-carboxylate. Amorphous solid. MS (ISP): 334.17 ([M+H]$^+$).

Example 35

(RS)-2-Phenyl-N-(4-(piperidin-3-yl)phenyl)-2H-1,2,3-triazole-4-carboxamide

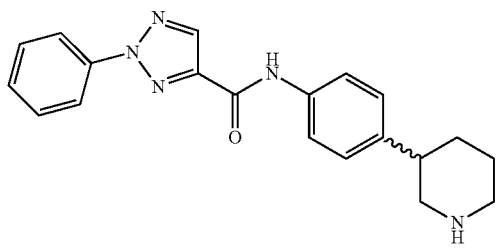 [SMILES: O=C(Nc1ccc(C2CCCNC2)cc1)c1cnn(-c2ccccc2)n1]

The title compound was obtained in analogy to example 1 using tert-butyl 3-(4-aminophenyl)piperidine-1-carboxylate instead of (S)-tert-butyl 2-(4-aminophenyl)morpholine-4-carboxylate. White solid. MS (ISP): 348.12 ([M+H]$^+$).

Example 36

(S)-1-(5-Bromopyridin-2-yl)-N-(4-(morpholin-2-yl)phenyl)-1H-1,2,3-triazole-4-carboxamide hydrochloride

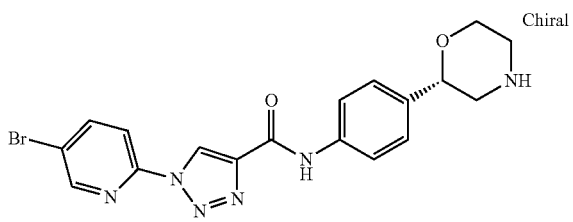 [SMILES: O=C(Nc1ccc([C@H]2CNCCO2)cc1)c1cn(-c2ccc(Br)cn2)nn1]

a) Methyl 1-(5-bromopyridin-2-yl)-1H-1,2,3-triazole-4-carboxylate

In a 10 ml round-bottomed flask, 6-bromotetrazolo[1,5-a]pyridine (209 mg, 1.05 mmol) was dissolved in a mixture of tetrahydrofuran (3.5 ml) and dimethylsulfoxide (0.06 ml) to give an orange solution. Methyl propiolate (265 mg, 276 μl, 3.15 mmol), copper (I) iodide (200 mg, 1.05 mmol) and 2,6-lutidine (225 mg, 245 μl, 2.1 mmol) were added and the reaction mixture was stirred at room temperature overnight. Water was added and the layers were separated using ethyl acetate. The organic layer was washed with 1 N hydrochloric acid and brine, dried over magnesium sulphate and filtered. The filtrate was concentrated under vacuum to yield a brown solid (300 mg), which was adsorbed on silica gel. Purification by flash chromatography (Silica gel, 20 g, 10 to 30% EtOAc in heptane) yielded a light grey solid (255 mg, 86%). MS (ISP): 283.4 ({$^{79}$Br} [M+H]$^+$), 285.4 ({$^{81}$Br} [M+H]$^+$).

b) 1-(5-Bromopyridin-2-yl)-1H-1,2,3-triazole-4-carboxylic acid

To a solution of methyl 1-(5-bromopyridin-2-yl)-1H-1,2,3-triazole-4-carboxylate (240 mg, 0.85 mmol) in a mixture of tetrahydrofuran (2.4 ml), methanol (2.4 ml) and water (2.4 ml) lithium hydroxide hydrate (107 mg, 2.54 mmol) was added. The solution was heated to 70° C. for 3 h. Most of the organic solvent was removed under reduced pressure. Water was added and the solution was extracted once with ether. Then 4 N hydrochloric acid was added to reach acidic pH. The product precipitated and the mixture was extracted three times with ethyl acetate. The organic layers were combined, dried (MgSO$_4$) and evaporated to yield a light brown solid (223 mg, 98%). MS (ISP): 269.4 ({$^{79}$Br} [M+H]$^+$), 271.4 ({$^{81}$Br} [M+H]$^+$).

c) (S)-tert-Butyl 2-(4-(1-(5-bromopyridin-2-yl)-1H-1,2,3-triazole-4-carboxamido)phenyl)morpholine-4-carboxylate Under argon, 1-(5-bromopyridin-2-yl)-1H-1,2,3-triazole-4-carboxylic acid (67.7 mg, 0.25 mmol) was suspended in dichloromethane (4 ml). Then 1-chloro-N,N'-trimethypropenylamine (38.6 mg, 0.038 ml, 0.289 mmol) was added dropwise and the mixture was stirred for 15 minutes at room temperature to form the acid chloride.

In a separate flask, (S)-tert-butyl 2-(4-aminophenyl)morpholine-4-carboxylate (70 mg, 0.25 mmol) was dissolved in dichloromethane (4 ml), ethyldiisopropylamine (81.3 mg, 0.1 ml, 0.63 mmol) was added. To this solution, the acid chloride was added dropwise and the mixture was stirred at room temperature for 2 hours.

The mixture was extracted with dichloromethane and ammonium chloride solution. The organic phase was washed with sodium carbonate solution and brine. It was dried over magnesium sulphate, filtered and concentrated in vacuo. The crude material was recrystallised from a mixture of ethyl acetate and dichloromethane to yield a white solid (72 mg, 54%). MS (ISP): 527.4 ({$^{79}$Br} [M–H]$^+$), 529.3 ({$^{81}$Br} [M–H]$^+$).

d) (S)-1-(5-Bromopyridin-2-yl)-N-(4-(morpholin-2-yl)phenyl)-1H-1,2,3-triazole-4-carboxamide hydrochloride (S)-tert-Butyl 2-(4-(1-(5-bromopyridin-2-yl)-1H-1,2,3-triazole-4-carboxamido)phenyl)morpholine-4-carboxylate (63 mg, 0.12 mmol) was dissolved in dioxane (0.5 ml) and a solution of HCl in dioxane (4 M, 0.36 ml, 1.44 mmol) was added. The reaction mixture was stirred for 2 hours at 60° C. After cooling, ether was added, the solid was filtered off, washed with ether and dried in vacuo at 60° C. to afford (S)-1-(5-bromopyridin-2-yl)-N-(4-(morpholin-2-yl)phenyl)-1H-1,2,3-triazole-4-carboxamide hydrochloride (48 mg, 87%) as a white solid. MS (ISP): 429.4 ({$^{79}$Br} [M–H]$^+$), 431.5 ({$^{81}$Br} [M–H]$^+$).

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Radioligand Binding Assay on Rat TAAR1
Membrane Preparation and Radioligand Binding.

HEK-293 cells stably expressing rat TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48'000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3[H]$—(S)-4-[(ethyl-phenyl-amino)-methyl]-4,5-dihydro-oxazol-2-ylamine (described in WO 2008/098857) was used at a concentration equal to the calculated Kd value, that was usually around 2.3 nM, resulting in the binding of approximately 0.2% of the radioligand and a specific binding representing approximately 85% of the total binding. Nonspecific binding was defined as the amount of $^3[H]$—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3[H]$—(S)-4-[(ethyl-phenyl-amino)-methyl]-4,5-dihydro-oxazol-2-ylamine at a concentration of 3.3×Kd in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

Radioligand Binding Assay on Mouse TAAR1
Membrane Preparation and Radioligand Binding.

HEK-293 cells stably expressing mouse TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48'000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3[H]$—(S)-4-[(ethyl-phenyl-amino)-methyl]-4,5-dihydro-oxazol-2-ylamine (described in WO 2008/098857) was used at a concentration equal to the calculated Kd value, that was usually around 0.7 nM, resulting in the binding of approximately 0.5% of the radioligand and a specific binding representing approximately 70% of the total binding. Nonspecific binding was defined as the amount of $^3[H]$—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3[H]$—(S)-4-[(ethyl-phenyl-amino)-methyl]-4,5-dihydro-oxazol-2-ylamine at a concentration of 3.3×Kd in nM and 500 µl of the membranes (resuspended at 60 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

The compounds show a $K_i$ value (µM) at mouse or rat TAAR1 in the range of <0.1 µM as shown in the table below.

| Example | $K_i$ (µM) mouse/rat |
|---|---|
| 1 | 0.0012/0.0013 |
| 2 | 0.0015/0.0008 |
| 3 | 0.0015/0.0268 |
| 4 | 0.0023/0.0342 |
| 5 | 0.0029/0.0211 |
| 6 | 0.0004/0.0002 |
| 7 | 0.0027/0.0002 |
| 8 | 0.0014/0.0008 |
| 9 | 0.0004/0.0006 |
| 10 | 0.0004/0.0002 |
| 11 | 0.0003/0.0004 |
| 12 | 0.0002/0.0002 |
| 13 | 0.0003/0.0006 |
| 14 | 0.0004/0.0032 |
| 15 | 0.0002/0.0001 |
| 16 | 0.0003/0.0002 |

-continued

| Example | $K_i$ (μM) mouse/rat |
|---------|----------------------|
| 17 | 0.0013/0.0174 |
| 18 | 0.0007/0.0016 |
| 19 | 0.0016/0.0388 |
| 20 | 0.0014/0.0019 |
| 21 | 0.0018/0.0293 |
| 22 | 0.0008/0.001 |
| 23 | 0.0011/0.0005 |
| 24 | 0.0013/0.0069 |
| 25 | 0.0014/0.0092 |
| 26 | 0.0011/0.0032 |
| 27 | 0.0068/0.0154 |
| 28 | 0.0034/0.0156 |
| 29 | 0.0009/0.0006 |
| 30 | 0.0032/0.0082 |
| 31 | 0.013/0.1066 |
| 32 | 0.0018/0.045 |
| 33 | 0.0049/0.0189 |
| 34 | 0.0032/0.001 |
| 35 | 0.0019/0.0017 |
| 36 | 0.0046/0.030 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula IA or IB and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety and attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| Item | Ingredients | mg/tablet | | | |
|------|-------------|-----------|---|---|---|
| | | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|------|-------------|------------|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

We claim:
1. A compound of formula

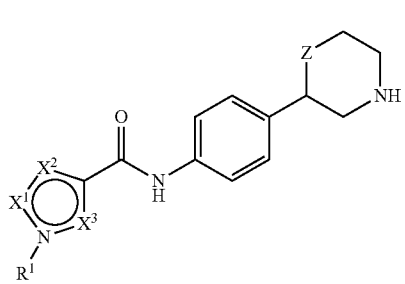

I wherein
$R^1$ is phenyl or pyridinyl, optionally substituted by halogen, lower alkyl, lower alkoxy, lower alkyl substituted by halogen and lower alkoxy substituted by halogen;

X¹ is —N= or CH;
X² is CR² or =N—;
X³ is —N= or CH;
  with the proviso that only two of X¹, X² or X³ are nitrogen;
wherein

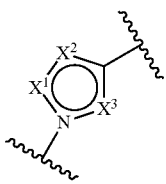

is a triazole group, selected from

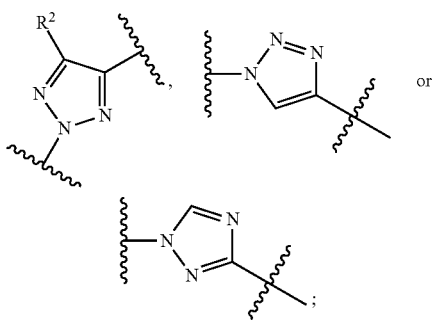

R² is hydrogen or lower alkyl;
Z is a bond, —O— or —CH₂—;
or a pharmaceutically suitable acid addition salts thereof.

2. A compound of formula IA according to claim 1,

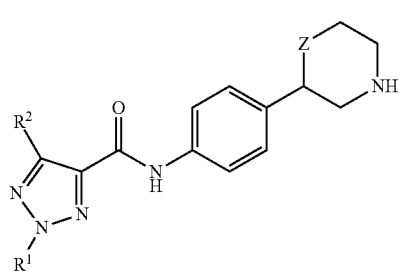

wherein
R¹ is phenyl or pyridinyl, optionally substituted by halogen, lower alkyl, lower alkoxy, lower alkyl substituted by halogen and lower alkoxy substituted by halogen;
R² is hydrogen or lower alkyl;
Z is a bond, —O— or —CH₂—;
or a pharmaceutically suitable acid addition salts thereof.

3. A compound of formula IA according to claim 1, wherein the compounds are
  (S)—N-(4-(Morpholin-2-yl)phenyl)-2-phenyl-2H-1,2,3-triazole-4-carboxamide
  (S)-5-Methyl-N-(4-(morpholin-2-yl)phenyl)-2-phenyl-2H-1,2,3-triazole-4-carboxamide
  (S)-2-(4-Chlorophenyl)-N-(4-(morpholin-2-yl)phenyl)-2H-1,2,3-triazole-4-carboxamide
  (R)-5-Methyl-N-(4-(morpholin-2-yl)phenyl)-2-phenyl-2H-1,2,3-triazole-4-carboxamide
  (R)—N-(4-(Morpholin-2-yl)phenyl)-2-phenyl-2H-1,2,3-triazole-4-carboxamide
  (S)-2-(4-Fluorophenyl)-N-(4-(morpholin-2-yl)phenyl)-2H-1,2,3-triazole-4-carboxamide
  (S)—N-(4-(Morpholin-2-yl)phenyl)-2-(4-(trifluoromethyl)phenyl)-2H-1,2,3-triazole-4-carboxamide
  (S)-2-(3-Fluorophenyl)-N-(4-(morpholin-2-yl)phenyl)-2H-1,2,3-triazole-4-carboxamide
  (S)-2-(3-Chlorophenyl)-N-(4-(morpholin-2-yl)phenyl)-2H-1,2,3-triazole-4-carboxamide
  (S)—N-(4-(Morpholin-2-yl)phenyl)-2-(3-(trifluoromethyl)phenyl)-2H-1,2,3-triazole-4-carboxamide
  (S)—N-(4-(Morpholin-2-yl)phenyl)-2-(4-(trifluoromethoxy)phenyl)-2H-1,2,3-triazole-4-carboxamide
  (S)-2-(4-(Difluoromethoxy)phenyl)-N-(4-(morpholin-2-yl)phenyl)-2H-1,2,3-triazole-4-carboxamide
  (S)—N-(4-(Morpholin-2-yl)phenyl)-2-p tolyl-2H-1,2,3-triazole-4-carboxamide hydrochloride
  (S)-2-(4-Methoxyphenyl)-N-(4-(morpholin-2-yl)phenyl)-2H-1,2,3-triazole-4-carboxamide
  (S)-2-(4-Ethoxyphenyl)-N-(4-(morpholin-2-yl)phenyl)-2H-1,2,3-triazole-4-carboxamide
  (S)—N-(4-(Morpholin-2-yl)phenyl)-2-m-tolyl-2H-1,2,3-triazole-4-carboxamide hydrochloride
  (S)—N-(4-(Morpholin-2-yl)phenyl)-2-(3-(trifluoromethoxy)phenyl)-2H-1,2,3-triazole-4-carboxamide
  (S)-2-(3-Methoxyphenyl)-N-(4-(morpholin-2-yl)phenyl)-2H-1,2,3-triazole-4-carboxamide
  (S)-2-(3-Methoxyphenyl)-N-(4-(morpholin-2-yl)phenyl)-2H-1,2,3-triazole-4-carboxamide
  (RS)-2-Phenyl-N-(4-(pyrrolidin-3-yl)phenyl)-2H-1,2,3-triazole-4-carboxamide or
  2-Phenyl-N-(4-(piperidin-3-yl)phenyl)-2H-1,2,3-triazole-4-carboxamide.

4. A compound of formula IB according to claim 1,

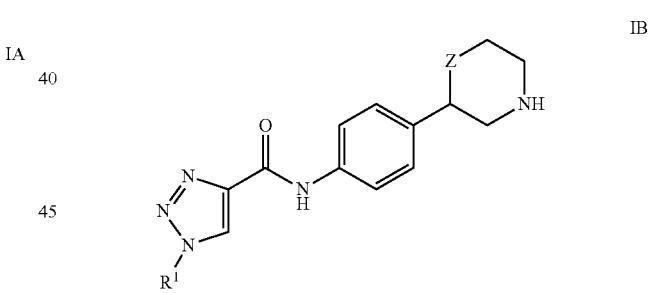

wherein
R¹ is phenyl or pyridinyl, optionally substituted by halogen, lower alkyl, lower alkoxy, lower alkyl substituted by halogen and lower alkoxy substituted by halogen;
Z is a bond, —O— or —CH₂—;
or a pharmaceutically suitable acid addition salts thereof.

5. A compound of formula IB according to claim 1, wherein the compounds are
  (S)-1-(4-(Difluoromethoxy)phenyl)-N-(4-(morpholin-2-yl)phenyl)-1H-1,2,3-triazole-4-carboxamide
  (S)-1-(4-Fluorophenyl)-N-(4-(morpholin-2-yl)phenyl)-1H-1,2,3-triazole-4-carboxamide
  (S)-1-(3-Fluorophenyl)-N-(4-(morpholin-2-yl)phenyl)-1H-1,2,3-triazole-4-carboxamide
  (S)—N-(4-(Morpholin-2-yl)phenyl)-1-(4-(trifluoromethoxy)phenyl)-1H-1,2,3-triazole-4-carboxamide
  (S)—N-(4-(Morpholin-2-yl)phenyl)-1-p-tolyl-1H-1,2,3-triazole-4-carboxamide hydrochloride (S)-1-(4-Methoxyphenyl)-N-(4-(morpholin-2-yl)phenyl)-1H-1,2,3-triazole-4-carboxamide
(S)-1-(4-Ethoxyphenyl)-N-(4-(morpholin-2-yl)phenyl)-1H-1,2,3-triazole-4-carboxamide
(S)—N-(4-(Morpholin-2-yl)phenyl)-1-m-tolyl-1H-1,2,3-triazole-4-carboxamide hydrochloride
(S)-1-(3-Methoxyphenyl)-N-(4-(morpholin-2-yl)phenyl)-1H-1,2,3-triazole-4-carboxamide
(S)-1-(3-Ethoxyphenyl)-N-(4-(morpholin-2-yl)phenyl)-1H-1,2,3-triazole-4-carboxamide
(S)—N-(4-(Morpholin-2-yl)phenyl)-1-(3-(trifluoromethoxy)phenyl)-1H-1,2,3-triazole-4-carboxamide
(S)-1-(3-(Difluoromethoxy)phenyl)-N-(4-(morpholin-2-yl)phenyl)-1H-1,2,3-triazole-4-carboxamide or
(RS)-1-(4-(Difluoromethoxy)phenyl)-N-(4-(pyrrolidin-3-yl)phenyl)-1H-1,2,3-triazole-4-carboxamide.

6. A compound of formula IC according to claim 1,

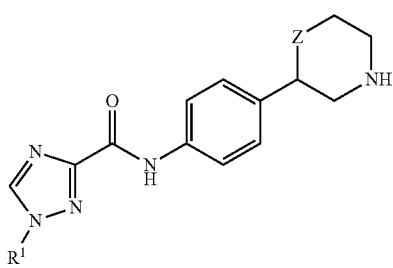

IC wherein
R$^1$ is phenyl or pyridinyl, optionally substituted by halogen, lower alkyl, lower alkoxy, lower alkyl substituted by halogen and lower alkoxy substituted by halogen;
Z is a bond, —O— or —CH$_2$—;
or a pharmaceutically suitable acid addition salts thereof.

7. A compound of formula IC according to claim 1, wherein the compound is
(S)-1-(4-(Difluoromethoxy)phenyl)-N-(4-(morpholin-2-yl)phenyl)-1H-1,2,4-triazole-3-carboxamide.

8. A process for the manufacture of a compound of formula I according to claim 1, which process comprises cleaving off the N-protecting group from compounds of formula

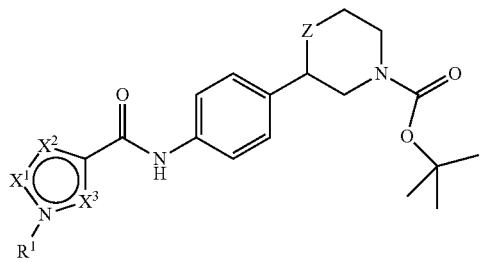

4 to form a compound of formula

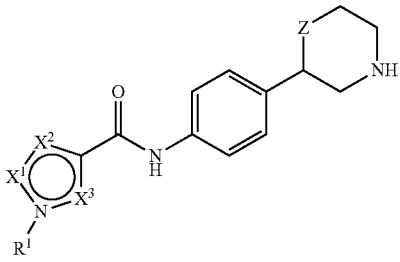

I wherein the definitions are as described above, and,
if desired, converting the compounds obtained into pharmaceutically acceptable acid addition salts.

9. A compound manufactured by a process according to claim 8.

10. A pharmaceutical composition comprising a compound according to claim 1 and a pharmaceutical acceptable carrier and/or adjuvant.

11. Compounds according to claim 1 for use as therapeutic active substances.

* * * * *